(12) United States Patent
Cueni et al.

(10) Patent No.: US 7,213,615 B2
(45) Date of Patent: May 8, 2007

(54) ROTATING VALVE

(75) Inventors: Hansjörg Emil Cueni, Stanstaad (CH); Heiner Scherrer, Büsserach (CH); Werner Döbelin, Reinach (CH)

(73) Assignee: CS Analytics AG, Beckenried (CH)

( * ) Notice: Subject to any disclaimer, the term of this patent is extended or adjusted under 35 U.S.C. 154(b) by 0 days.

(21) Appl. No.: 10/551,751

(22) PCT Filed: Apr. 2, 2004

(86) PCT No.: PCT/CH2004/000207

§ 371 (c)(1),
(2), (4) Date: Jan. 9, 2006

(87) PCT Pub. No.: WO2004/088303

PCT Pub. Date: Oct. 14, 2004

(65) Prior Publication Data
US 2006/0191581 A1    Aug. 31, 2006

(30) Foreign Application Priority Data
Apr. 3, 2003   (CH) .................................. 0594/03

(51) Int. Cl.
*F16K 11/074*  (2006.01)
(52) U.S. Cl. .................. 137/625.46; 73/61.55
(58) Field of Classification Search .......... 137/625.46; 73/61.55
See application file for complete search history.

(56) References Cited

U.S. PATENT DOCUMENTS

| 3,477,207 | A |   | 11/1969 | Auger |
|---|---|---|---|---|
| 4,625,569 | A |   | 12/1986 | Toei et al. |
| 5,010,921 | A | * | 4/1991 | Nohl ................... 137/625.46 |
| 6,672,336 | B2 | * | 1/2004 | Nichols ................ 137/625.46 |
| 6,874,354 | B2 | * | 4/2005 | Cueni et al. ............. 73/61.55 |
| 6,997,213 | B1 | * | 2/2006 | Towler et al. ......... 137/625.46 |

FOREIGN PATENT DOCUMENTS

| JP | 62-56858 | 3/1987 |
|---|---|---|
| WO | WO 02/12878 | 2/2002 |

\* cited by examiner

*Primary Examiner*—John Fox
(74) *Attorney, Agent, or Firm*—Ladas & Parry LLP

(57) ABSTRACT

The rotating valve for high performance liquid chromatography (HPLC) has a stator with connections for the solvent reservoirs, pumps, chromatography columns etc. and a disc-shaped rotor with connecting grooves on the front face for selectively connecting different connections to one another. Said grooves are evenly distributed on two concentrical circles. The connecting grooves on the front face of the rotor are configured in the form of circular segments and are arranged in such a way that fife connections are simultaneously connected to one another in defined positions of the rotor in each circle.

1 Claim, 2 Drawing Sheets

ROTATING VALVE

The invention is related with a rotating valve for high performance liquid chromatography (HPLC) having a stator with connections for the solvent reservoirs, pumps, chromatography columns etc. and bore-holes leading from the connections to orifices in a contact surface, as well as a disc-shaped rotor with connecting grooves in its front face for selectively connecting different orifices with each other.

With regard to valves for the high performance liquid chromatography as for HPLC pumps great effort is made since long time to achieve as constant transport pressures and flow rates as possible by reducing switching effects. The smaller the flow rates get, the more disturbing becomes the effect of dead volumes, which however cannot be fully eliminated in valves. Equally undesired are strong pressure pulsations which however increase with continuously higher working pressures due to the compressibility. Both disturbances result in peak broadening and other errors which deteriorate the measuring accuracy and the resolution. Presently requested flow rates are in the range of 10 μl to 200 um and desired pressures reach already up to 800 bar. Satisfactory achievement of these requirements with conventional valves is possible not any more or only with high effort.

It is therefore the object of the invention to provide a valve with which these negative effects can be reduced with reasonable effort.

According to the invention this is achieved with a valve of the type mentioned initially in which the orifices in the contact surface are distributed equally over two concentrical circles and the connecting grooves in the rotor front face are configured as an arc of a circle and are arranged such that in defined rotor positions fife orifices are simultaneously interconnected on each circle.

In the following preferred embodiments of the invention are described with reference to the accompanying drawings.

It is shown in

Figure 1:
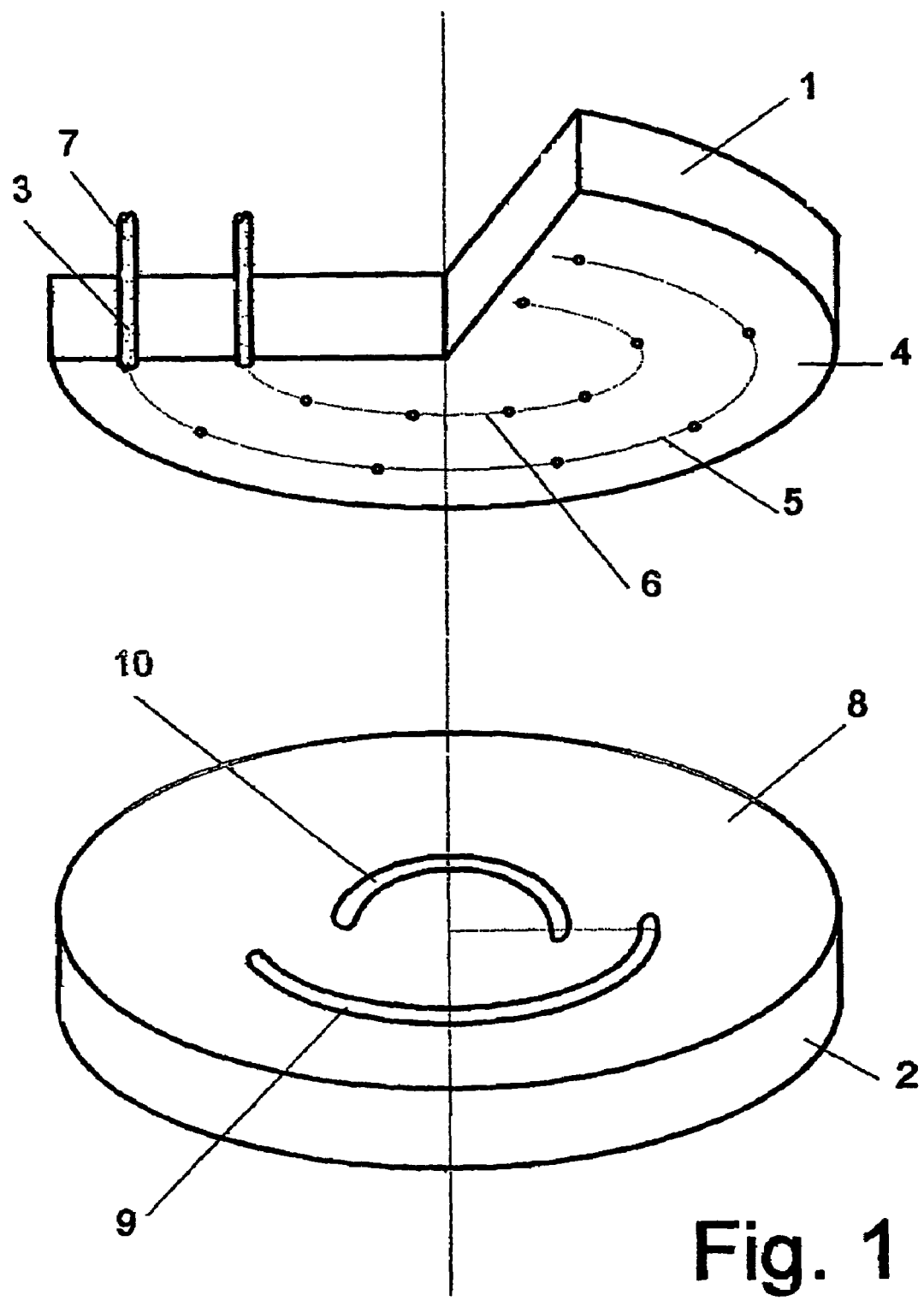

FIG. 1 a schematic diagram of a rotating valve according to the invention

FIG. 2–6 a binary gradient pump system with a valve according to the invention in different switching positions.

The rotating valve schematically shown in FIG. 1 consists essentially of a disc-shaped stator 1 and an equally disc-shaped rotor 2. In the stator altogether eighteen through-holes 3 are arranged such that their orifices at the contact surface 4 facing the rotor are equally distributed over two concentrical circles 5,6. At the backside connections 7 are provides for connecting lines to pumps, solvent reservoirs, chromatography columns etc.

The rotor 2 has on its front surface 8 facing the stator two arc-shaped grooves 9,10 which in the assembled state of the valve, when the front face of the rotor is pressed against the contact face of the stator, extend along the circles on which the orifices of the holes 3 are positioned. The length of the grooves is dimensioned such that each can connect simultaneously five orifices of the holes on its respective circle.

With nine hole orifices per circle the angular distance between two orifices comes to 40°, so that the grooves need to extend over an angle of about 160° to connect five orifices. They are arranged such that each of them has one end at one common angular position, from where one of them extends in clockwise and the other in counter-clockwise direction.

Figure 2:
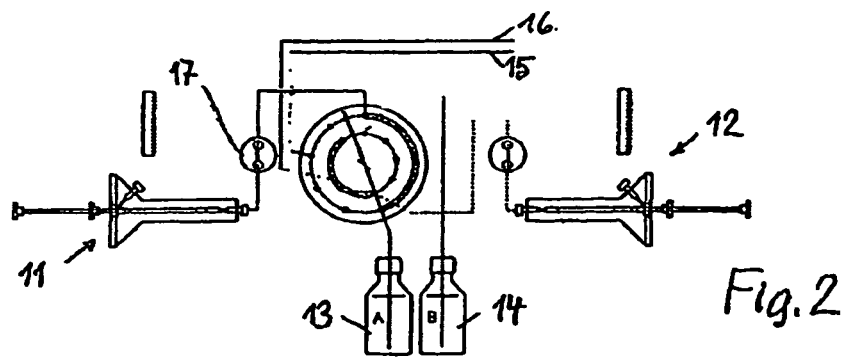

In the configuration shown in FIG. 2 the valve exhibited in schematic top view is connected with two piston pumps 11,12, two solvent reservoirs 13,14, and two exits to a gradient system for the solvent feeding to a chromatography column. At the connection of the outer circle 5 located in the angular position 0° a pump 11 is connected for the solvent A contained in reservoir 13. The respective 0° connection of the inner circle is connected with the other reservoir 14 containing the solvent B. The second reservoir 13 with the solvent A is connected to the connection located in angular position 160° of the outer circle. To the respective connection of the inner circle the second pump 12 for the solvent B is connected. Eventually, the connection at 280° of the outer circle and the connection at 240° of the inner circle lead to the exit towards the column. These two exits are combined in a mixer (not shown) as usual.

In the rotor position shown the connection of pump 11 for solvent A is linked with the connection for the respective reservoir 13 via the outer groove. Thus, in this position pump 11 can draw solvent A. At the same time the connection for the other pump 12 for solvent B is linked via the inner groove to the connection for the respective exit 16. Thus, in this rotor position this pump can transfer the solvent B contained in it towards the exit or column respectively.

Between the pumps and the respective valve connections highly sensitive pressure transducers 17 are arranged the signals of which are used for pump and valve control.

Figure 3:
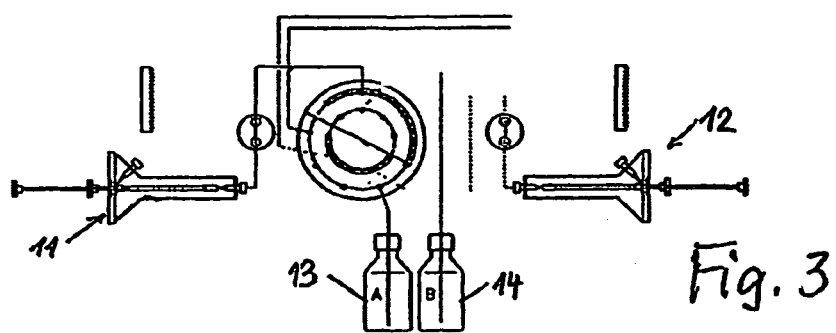

FIG. 3 shows the same configuration in which the rotor is rotated by one angular position in counter-clockwise direction after the end of the drawing process of pump 11. Now, no other connection except the pump connection runs into the outer groove, so that pump 11 can compress the previously drawn solvent A until the necessary or desired transport pressure is reached. For the solvent B nothing has changed by the switching. The other pump 12 is still connected via groove 10 to the exit 16 and continues to transport uniformly.

Figure 4:
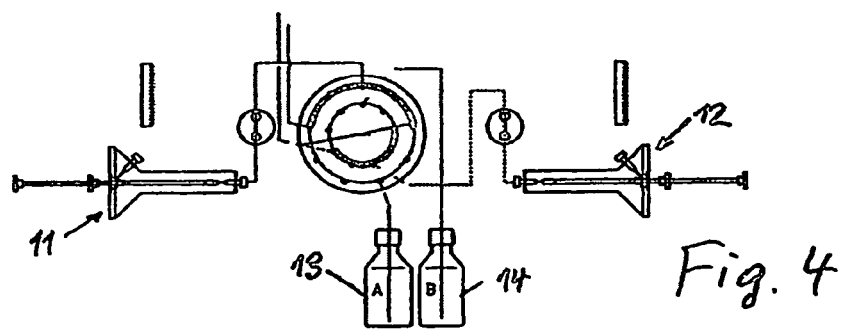
Figure 6:
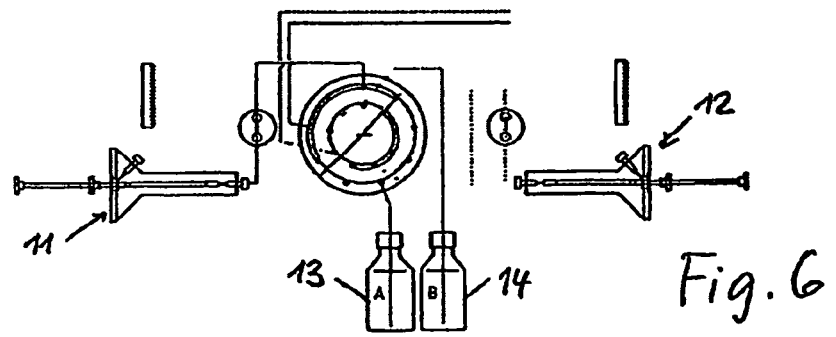

When solvent A has reached the desired pressure and the transport of both solvents is to start, the rotor is rotated by a further angular step in counter-clockwise direction into the position shown in FIG. 4. In this position both pumps are connected with both exits. The mixing ratio of the two solvents is controlled via the forward movement of the two pumps.

Figure 5:
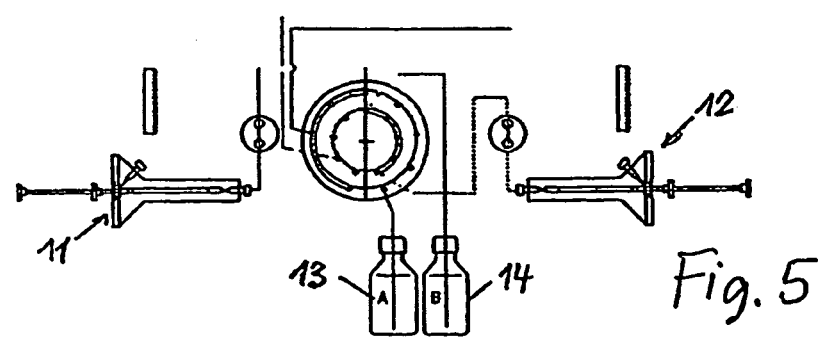

When the transport of solvent B by pump 12 is finished and only solvent A is still transported, the rotor is rotated by two angular steps in counter-clockwise direction into the position shown in FIG. 5. In this position pump 11 is still connected to exit 15 via the outer groove 9, while the inner groove 10 connects pump 12 to reservoir 14 of solvent B. Pump 12 can now again refill with solvent B.

By rotor rotation in backward direction, i.e. clockwise, the respective steps take place in opposite sequence. After the end of the filling procedure the rotor is turned in clockwise direction by one angular step. In this position shown FIG. 6 the inner groove does not provide any connections so that pump 12 can pre-compress the solvent to the desired transport pressure. For pump 11 nothing has changed, i.e. it can continue to transport uniformly. There are further rotor turns in clockwise direction until the situation according to FIG. 2 is reached again.

The invention claimed is:

1. Rotating valve for high performance liquid chromatography (HPLC) having a stator with connections for the solvent reservoirs, pumps, chromatography columns etc. and bore-holes leading from the connections to orifices in a contact surface, as well as a disc-shaped rotor with connecting grooves in its front face for selectively connecting different orifices with each other, characterized in that the orifices in the contact surface are distributed equally over two concentrical circles and the connecting grooves in the rotor front face are configured as an arc of a circle and are arranged such that in defined rotor positions five orifices are simultaneously interconnected on each circle.

* * * * *